(12) United States Patent
Schmitz et al.

(10) Patent No.: US 9,221,776 B2
(45) Date of Patent: Dec. 29, 2015

(54) EPOXIDATION PROCESS

(71) Applicant: Scientific Design Company, Inc., Little Ferry, NJ (US)

(72) Inventors: Andrew D. Schmitz, Hackensack, NJ (US); William Crudge, Upper Saddle River, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

(21) Appl. No.: 14/578,803

(22) Filed: Dec. 22, 2014

(65) Prior Publication Data

US 2015/0175565 A1 Jun. 25, 2015

Related U.S. Application Data

(60) Provisional application No. 61/920,198, filed on Dec. 23, 2013.

(51) Int. Cl.
  *C07D 301/03* (2006.01)
  *C07D 301/10* (2006.01)

(52) U.S. Cl.
  CPC .................................. *C07D 301/10* (2013.01)

(58) Field of Classification Search
  CPC ..................................................... C07D 301/03
  USPC ......................................................... 549/536
  See application file for complete search history.

(56) References Cited

U.S. PATENT DOCUMENTS

| | | | |
|---|---|---|---|
| 2,279,469 A | 4/1942 | Law et al. | |
| 3,563,914 A | 2/1971 | Wattimena | |
| 3,702,259 A | 11/1972 | Nielsen | |
| 4,761,394 A | 8/1988 | Lauritzen | |
| 4,766,105 A | 8/1988 | Lauritzen | |
| 4,908,343 A | 3/1990 | Bhasin | |
| 5,011,807 A | 4/1991 | Hayden et al. | |
| 5,057,481 A | 10/1991 | Bhasin | |
| 5,099,041 A | 3/1992 | Hayden et al. | |

(Continued)

FOREIGN PATENT DOCUMENTS

| | | |
|---|---|---|
| EP | 0352850 B1 | 1/1990 |
| GB | 1055147 | 1/1967 |
| WO | 2004/002971 A1 | 1/2004 |

OTHER PUBLICATIONS

International Search Report and Written Opinion dated Apr. 1, 2015 received in corresponding foreign International Application No. PCT/US2014/071816.

*Primary Examiner* — T. Victor Oh
(74) *Attorney, Agent, or Firm* — Scully, Scott, Murphy & Presser, P.C.

(57) ABSTRACT

A method for the epoxidation of an olefin comprising reacting a feed gas composition containing an olefin, oxygen, and a halocarbon moderator having a first moderator concentration $M_1$ in the presence of an epoxidation catalyst at a first temperature $T_1$; increasing the first temperature to a second temperature $T_2$; and increasing the first moderator concentration to a second moderator concentration $M_2$, wherein the second moderator concentration is defined by:

$$M_2 = M_1(1+r)^{T_2-T_1}$$

wherein the temperature has the units of degrees Celsius, and r is a constant factor which is in the range of from 0.001% to 100%.

13 Claims, 3 Drawing Sheets

(56) References Cited

U.S. PATENT DOCUMENTS

| | | |
|---|---|---|
| 5,102,848 A | 4/1992 | Soo et al. |
| 5,187,140 A | 2/1993 | Thorsteinson et al. |
| 5,407,888 A | 4/1995 | Herzog et al. |
| 7,102,022 B2 | 9/2006 | Evans et al. |
| 7,485,597 B2 | 2/2009 | Lockemeyer et al. |
| 7,657,331 B2 | 2/2010 | Chipman et al. |
| 7,657,332 B2 | 2/2010 | Chipman et al. |
| 2007/0037991 A1 | 2/2007 | Rizkalla |
| 2007/0129557 A1 | 6/2007 | Chipman et al. |
| 2011/0152548 A1 | 6/2011 | Sachs et al. |
| 2013/0096330 A1 | 4/2013 | Al-ahmadi et al. |

EPOXIDATION PROCESS

CROSS REFERENCE TO RELATED APPLICATION

The present invention claims the benefit of U.S. Provisional Patent Application No. 61/920,198 filed Dec. 23, 2013, the entire content and disclosure of which is incorporated herein by reference.

BACKGROUND OF THE INVENTION

Though present in natural settings at minute quantities, ethylene oxide ("EO") was first synthesized in a laboratory setting in 1859 by French chemist Charles-Adolphe Wurtz using the so-called "chlorohydrin" process. However, the usefulness of ethylene oxide as an industrial chemical was not fully understood in Wurtz's time; and so industrial production of ethylene oxide using the chlorohydrin process did not begin until the eve of the First World War due at least in part to the rapid increase in demand for ethylene glycol (of which ethylene oxide is an intermediate) as an antifreeze for use in the rapidly growing automobile market. Even then, the chlorohydrin process produced ethylene oxide in relatively small quantities and was highly uneconomical.

The chlorohydrin process was eventually supplanted by another process, the direct catalytic oxidation of ethylene with oxygen, the result of a second breakthrough in ethylene oxide synthesis, discovered in 1931 by another French chemist Theodore Lefort. Lefort used a solid silver catalyst with a gas phase feed that included ethylene and utilized air as a source of oxygen.

In the eighty plus years since the development of the direct oxidation method, the production of ethylene oxide has increased so significantly that today it is one of the largest volume products of the chemicals industry, accounting, by some estimates, for as much as half of the total value of organic chemicals produced by catalytic heterogeneous oxidation. Worldwide production in the year 2000 was about 15 billion tons. (About two thirds of the ethylene oxide produced is further processed into ethylene glycol, while about ten percent of manufactured ethylene oxide is used directly in applications such as vapor sterilization.)

The growth in the production of ethylene oxide has been accompanied by continued intensive research on ethylene oxide catalysis and processing, which remains a subject of fascination for researchers in both industry and academia. Of particular interest in recent years has been the proper operating and processing parameters for the production of ethylene oxide using so-called "high selectivity catalysts", that is Ag-based epoxidation catalysts that contain small amounts of "promoting" elements such as rhenium and cesium.

Catalytic oxidation of ethylene to ethylene oxide is usually practiced as a gas phase process in which the feed is contacted in the gas phase with the catalyst present as a solid material. The catalyst is typically positioned in a tubular, packed-bed reactor, and the reactor is typically equipped with heat exchange facilities to heat or cool the catalyst. Rather than directly measuring the catalyst temperature, the temperature of the process is typically determined by measuring the "coolant temperature" that is, the temperature of the coolant outside the tubes.

Halogen-containing compounds, especially chlorohydrocarbons, have long been used in the feed mixture for the gas phase production of ethylene oxide (see e.g., Law et al., U.S. Pat. No. 2,279,469, issued Apr. 14, 1942; U.K. Patent No. 1,055,147 issued Jan. 18, 1967, and Lauritzen, EPO Patent No. 0 352 850 B1, issued Jan. 19, 1994). The added halogen-containing compound has been variously known as an "inhibitor", "modifier", "moderator", "anti-catalyst", and "promoter", and is herein called a "moderator".

The moderator plays a key role in maintaining the catalyst's activity and selectivity for producing ethylene oxide. This is especially true for rhenium-containing, highly selective catalysts where optimum performance can only be obtained within a narrow moderator concentration range within the feed mixture. Furthermore, this optimum moderator concentration range is not fixed, but it changes with temperature. Catalyst performance deteriorates with time, so temperature is generally increased with time to maintain a constant rate of ethylene oxide production. The moderator concentration must therefore be incrementally increased with temperature to keep the catalyst operating at peak efficiency.

The highly selective catalyst's efficiency for producing ethylene oxide in catalytic oxidation of ethylene is very important. This efficiency is a combination of catalyst selectivity and catalyst activity. Selectivity is defined as the amount of ethylene oxide produced for a given amount of ethylene (or oxygen) reacted on the catalyst; whereas, the activity is customarily expressed in terms of the reactor coolant temperature required for production of ethylene oxide at a given rate. The rate of ethylene oxide production is commonly expressed in terms of the amount of ethylene oxide produced per unit volume (or mass) of the catalyst per unit time.

Because the selectivity and activity of the highly selective catalyst are both very sensitive to the concentration of moderator in the reactor feed, the moderator concentration must be carefully tuned to maximize the efficiency of the catalyst. Historically, operators of the highly selective catalyst have attempted to optimize the moderator concentration by trial and error. The skilled operator would make an incremental change to the moderator concentration, up or down, and then wait to see the change in catalyst efficiency. If catalyst efficiency improved, then the operator would continue making incremental changes in the same direction until maximum ethylene oxide selectivity could be obtained at the lowest reactor coolant temperature. If catalyst efficiency had not improved with the change in moderator concentration, then the operator had to reverse the steps and attempt to optimize catalyst efficiency by moving moderator concentration in the opposite direction. This optimization process is painstakingly slow and tedious and generally must be executed by someone skilled in the art of operating the highly selective catalyst. The optimization process can be especially difficult or impossible if the temperature is fluctuating.

Increasing the moderator concentration above the optimum generally causes selectivity to decrease, but because the catalyst function may degrade more quickly at higher temperatures, it is sometimes desirable to increase the moderator concentration still further, anyway, and to suffer some selectivity loss in exchange for operating the catalyst at a lower temperature.

Temperature can increase or decrease when a change is made to the operating conditions of the catalytic oxidation of ethylene to ethylene oxide process. Temperature is generally increased over the service life of the catalyst to compensate for the loss in the catalyst's activity. Irrespective of the cause, the moderator concentration must be re-optimized every time the temperature changes. Again, this means making small adjustments to the moderator concentration until it appears that maximum catalyst operating efficiency has been reestablished. Even for persons skilled in the art, these repetitive, incremental re-optimizations are difficult and make it inherently difficult to keep the catalyst operating at peak efficiency and likewise, to maintain high efficiency in the overall catalytic process.

The present invention solves this problem by precisely correlating the change in moderator concentration with the change in temperature to keep the highly-selective catalyst operating at peak efficiency in the oxidation of ethylene to ethylene oxide. With the inventive correlation, there is no longer need to search for the new optimum by a skilled operator, making iterative, incremental changes to the moderator concentration, hoping to find the new optimum. When the temperature changes, the moderator concentration in the feed is simply adjusted, manually or automatically, to the new level given by the inventive correlation. This action can be completed by any operator, because it requires no special skill.

In fact, the invention is sufficiently analytic that it can be automated or controlled by a digital control system. Techniques for such automation of the moderator levels have been proposed in the prior art. For example, U.S. Pat. Nos. 7,657,331 and 7,657,332 recite specific formulas and ratios to predict what the optimal modifier (herein, moderator) levels should be, making use of a "Q value" for calculating the correct chloride concentration. This Q value is the ratio of the total "effective" moderator to the total "effective" hydrocarbon. The "effective" hydrocarbon value is determined by multiplying the molar concentration for each species of hydrocarbon by a correction factor that (according to theory) accounts for the differences in the ability of the different hydrocarbons to remove/strip reaction modifier from the surface of the catalyst; while the "effective" moderator value is determined by multiplying the molar concentration for each species of moderator by a correction factor that (again, according to theory) accounts for the number of "active species" present in a specific moderator. These correction factors are determined for each individual hydrocarbon and moderator by what is, apparently, a complicated process of experimental trial and error; however, the process for determining these correction factors is not set out with specificity in the aforementioned patents nor any actual examples of the procedure presented.

Within this same prior art, it is also taught that "when the reaction temperature is increased or decreased, the position of the selectivity curve for the modifier [moderator] shifts towards a higher value of Q or a lower value of Q, respectively, proportionally with the change in the reaction temperature." Similarly, U.S. Pat. Nos. 7,102,022 and 7,485,597 also teach that "deviations from the optimum selectivity which would result from a change in temperature may be reduced or even prevented by adjusting the value of Q proportionally with the change in catalyst temperature." These four examples teach that Q must be adjusted in a linear fashion with temperature according to the relationship:

$$Q_2 = Q_1 + B(T_2 - T_1)$$

where T is temperature, Q is the ratio of the total effective moderator to the total effective hydrocarbon and B is the linear proportionality constant.

The present invention shows that optimum moderator concentration does not vary in a linear fashion with temperature. For a highly selective catalyst in the catalytic oxidation of ethylene to ethylene oxide, the relationship between optimum moderator concentration and temperature shows distinct curvature and is predominantly exponential. The present invention accounts for this curvature and therefore overcomes the inadequacy of the prior art. The present invention can now be used in straightforward manner to maintain optimum selectivity when the temperature of the catalytic process changes.

For maintaining optimum moderator concentration, the cases cited from the prior art require that correction factors for each species of moderator and hydrocarbon species in the feed gas be determined and also requires these correction factors be used in detailed calculations for determining Q. Aside from the values of correction factors for the hydrocarbons and moderators that are specifically set forth in the specification, there is no general procedure detailed in the description to determine the correction factors for the hydrocarbons and moderators. Moreover, it is not clear how broadly the measurement of correction factors may be applied across the variance in operating parameters and circumstances that are experienced under actual service conditions for the highly selective catalyst. Specifically, it is not clear if a correction factor measured with respect to a first composition of reaction modifiers and hydrocarbons and a first catalyst and catalyst surface, can be subsequently used later with a different composition of reaction modifiers and hydrocarbons and a different catalyst and catalyst surface. On yet a more general level, there is no evidence to support the theory that is the basis for these patents regarding the correlation of correction factors to the stripping behavior of hydrocarbons, and the ability of moderator actives to "split" off from compounded heteroatoms. The present invention overcomes these apparent limitations, requiring neither determination of correction factors nor calculation of Q.

EP Patent No. 0 352 850 B1 teaches that "after the catalyst has 'lined-out' and normal operating conditions are reached," that the "chlorohydrocarbon moderator [be] slowly increased over the run time at an average rate of increase of at least 0.5% per month during the operation of the catalyst, more preferably at an average rate of increase of at least 1% per month and even more preferably at an average rate of increase of at least 3% per month and yet even more preferably at an average rate of increase of at least 5% per month." While EP 0 352 850 prescribes the need to increase the concentration of the moderator in the feed with operation time, it fails to provide an approach for the critical element of maintaining optimum moderator concentration with temperature change.

According to the prior art, maintaining the most preferred moderator levels is a laborious and time consuming process. It would require considerable expertise among operational staff, but such staff expertise is not always available, particularly in commercial, continuously operating ethylene oxide plants. Rather than requiring such expertise to always be available, it would be highly desirable to develop a process for controlling moderator levels that is sufficiently analytic that it can automated or even programmed into a digital control system.

Given the disadvantages of the currently practiced methods, as well as the importance of maintaining proper moderator level to the performance of the highly selective catalysts, there is a continuing need for a process for controlling moderator levels that is sufficiently analytic that it can be automated or programmed into a digital control system and yet can be practically implemented at plant scale without the need for extensive and speculative empirical manipulation. This is accomplished in the present invention.

SUMMARY OF THE INVENTION

The present invention relates to a method for the epoxidation of an olefin comprising: reacting a feed gas composition containing an olefin, oxygen, and a halocarbon moderator having a first moderator concentration $M_1$ in the presence of an epoxidation catalyst at a first temperature $T_1$; increasing the first temperature to a second temperature $T_2$; and increasing the first moderator concentration to a second moderator concentration $M_2$, wherein the second moderator concentration is defined by the equation:

$$M_2 = M_1(1+r)^{T_2-T_1}$$

wherein the temperature has the units of degrees Celsius, and r is a constant factor which is in the range of from 0.001% to 100%.

DETAILED DESCRIPTION OF THE INVENTION

All parts, percentages and ratios used herein are expressed by volume unless otherwise specified. All documents cited herein are incorporated by reference. The present invention is directed to the gas phase oxidation of olefin to form an olefin oxide by contacting a rhenium-containing silver-based catalyst in a reactor with a feed that contains at least oxygen, an olefin, and a moderator. It has been discovered in the present invention that optimum oxidation catalyst efficiency is obtained by accompanying a change in reactor (or reaction) temperature with a change in moderator concentration that is calculated according to the inventive exponential relationship. Optimum oxidation efficiency is defined as the combination of maximum olefin oxide selectivity and lowest reactor coolant temperature. Specifically, when reacting a feed gas comprising olefin, oxygen, and a moderator at a first optimized moderator concentration $M_1$ and at a first temperature $T_1$, then when the first temperature is changed to a second temperature $T_2$, the optimal second moderator concentration $M_2$ can be determined by the following exponential relationship:

$$M_2 = M_1(1+r)^{T_2-T_1}$$

In the inventive relationship, the values of M, T, r and k must all be greater than zero, and the units of T are degrees Celsius. For the oxidation of ethylene to ethylene oxide, the moderator concentration in the feed varies, most commonly, between 0.001 and 100 ppmv (parts per million on a volumetric basis). Temperatures T over the highly selective catalyst are commonly in the range from 190° C. to 300° C., preferably from 220° C. to 280° C. Suitable values for the moderator control factor r are from 0.001% to 100%. Values between 0.1% and 10% are preferred, and values between 2% and 8% are especially preferred, and values of about 4% are most especially preferred.

This performance-optimizing relationship between temperature and moderator concentration is applicable over the entire commercially-relevant temperature range of an epoxidation process and is independent of any specific feed gas composition. In implementing this performance-optimizing relationship, the moderator concentration levels can be adjusted either automatically, by being programmed into a digital control system or some similar hardware system, or manually, by use of routine and simple arithmetic calculations without the need of the continued supervision of highly-skilled operating staff. Unlike other previous automated control systems, this system does not require sophisticated analytical equipment or a complicated theoretical work-up in order to be effective.

As described, the relationship between moderator concentration in the feed and temperature is exponential. Those skilled in the art will recognize that the inventive relationship can be written in various alternative forms. For example, taking logarithms (to any base) of both sides of the exponential form gives the following equivalent relationships:

$$\log M_2 = \log M_1 + (T_2 - T_1)\log(1+r)$$

$$\log\left(\frac{M_2}{M_1}\right) = (T_2 - T_1)\log(1+r)$$

This last form of the inventive relationship shows that the value of r can be determined empirically by linear regression of a plot of $\log(M_2/M_1)$ on $(T_2-T_1)$.

The inventive relationship can also be written as the following exponential function:

$$M_2 = M_1 e^{k(T_2-T_1)}$$

where k is related to r as follows $$k = \ln(1+r)$$

Highly Selective Silver-Based Epoxidation Catalyst

The highly selective oxidation catalyst includes a carrier, and at least a catalytically effective amount of silver or a silver-containing compound, a promoting amount of cesium or a cesium-containing compound, and a promoting amount of rhenium or a rhenium-containing compound. Optionally present is a promoting amount of one or more other alkali metals or alkali-metal-containing compounds, namely Li, Na, K or Rb.

The carrier employed in this invention may be selected from a large number of solid, refractory materials that may be porous and may provide the preferred pore structure. Alpha-alumina is well known to be useful as a catalyst carrier for the epoxidation of an olefin and is the preferred carrier. The carrier may comprise materials such as alpha-alumina, charcoal, pumice, magnesia, zirconia, titania, kieselguhr, fuller's earth, silicon carbide, silica, silicon carbide, clays, artificial zeolites, natural zeolites, silicon dioxide and/or titanium dioxide, ceramics and combination thereof. The preferred carrier comprises at least about 95 wt. % alpha-alumina and preferably, at least about 98 wt. % alpha-alumina.

Regardless of its composition, the carrier is usually shaped into particles, chunks, pieces, pellets, rings, spheres, wagon wheels, cross-partitioned hollow cylinders, and the like, of a size suitable for employment in a fixed-bed epoxidation reactor. The carrier particles will preferably have equivalent diameters in the range from about 3 mm to about 12 mm, and more preferably in the range from about 5 mm to about 10 mm. Equivalent diameter is the diameter of a sphere having the same external surface (i.e., neglecting the surface within the pores of the particle) to volume ratio as the carrier particles being employed.

Suitable carriers are available from Saint-Gobain Norpro Co., Sud Chemie AG, Noritake Co., CeramTec AG, and Industrie Bitossi S.p.A. Without being limited to the specific compositions and formulations contained therein, further information on carrier compositions and methods for making carriers may be found in U.S. Patent Publication No. 2007/0037991.

In order to produce a highly selective catalyst for the oxidation of an olefin to an olefin oxide, a carrier having the above characteristics is then provided with a catalytically effective amount of silver on its surface. The catalyst is prepared by impregnating the carrier with a silver compound, complex or salt dissolved in a suitable solvent sufficient to cause deposition of silver or a silver-precursor compound onto the carrier. Preferably, an aqueous silver solution is used.

A promoting amount of a rhenium component, which may be a rhenium-containing compound or a rhenium-containing complex, is also deposited on the carrier, either prior to, coincidentally with, or subsequent to the deposition of the silver. The rhenium promoter may be present in an amount from about 10 ppm to about 10,000 ppm, preferably from about 50 ppm to about 5000 ppm, and more preferably from about 100 ppm to about 1000 ppm based on the weight of the total catalyst including the carrier, when measured as rhenium metal.

A promoting amount of a cesium component, which may be a cesium-containing compound or a cesium-containing complex, may also be deposited on the carrier, either prior to, coincidentally with, or subsequent to the deposition of the silver. The cesium promoter may be present in an amount from about 10 ppm to about 3000 ppm, more preferably from about 15 ppm to about 2000 ppm, and even more preferably from about 20 ppm to about 1500 ppm by weight of the total catalyst, when measured as cesium metal.

Other components which may also be deposited on the carrier either prior to, coincidentally with, or subsequent to the deposition of the silver, rhenium and cesium are promoting amounts of another alkali metal or mixtures of two or more additional alkali metals, as well as optional promoting amounts of a Group IIA alkaline earth metal component or mixtures of two or more Group IIA alkaline earth metal components, and/or another metal component or mixtures of two or more metal components, all of which may be in the form of metal ions, metal compounds, metal complexes and/or metal salts dissolved in an appropriate solvent, and/or a non-metal component or mixtures of two or more non-metal components, all of which may be in the form of non-metal ions, non-metal compounds, non-metal complexes and/or non-metal salts dissolved in an appropriate solvent. The carrier may be impregnated at the same time or in separate steps with the various catalyst promoters. The particular combination of carrier, silver, alkali metal promoter(s), rhenium component, and optional additional promoter(s) of the instant invention will provide an improvement in one or more catalytic properties over the same combination of silver and carrier and none, or only one of the promoters.

As used herein the term "promoting amount" of a certain component of the catalyst refers to an amount of that component that works effectively to improve the catalytic properties of the catalyst when compared to a catalyst that does not contain that component. The exact concentrations employed, of course, will depend on, among other factors, the desired silver content, the nature of the carrier, the viscosity of the liquid, and solubility of the particular compound used to deliver the promoter into the impregnating solution. Examples of catalytic properties include operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished.

Suitable additional alkali metal promoters may be selected from lithium, sodium, potassium, rubidium or combinations thereof. The amount of additional alkali metal deposited or present on the carrier is to be a promoting amount. Preferably, the amount ranges from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, when measured as the alkali metal.

Suitable alkaline earth metal promoters comprise elements from Group IIA of the Periodic Table of the Elements, which may be beryllium, magnesium, calcium, strontium, and barium or combinations thereof. Suitable additional metal promoters may comprise elements from Groups IVA, VA, VIA, VIIA and VIIIA of the Periodic Table of the Elements, and combinations thereof. Most preferably the additional metal comprises an element selected from Groups IVA, VA or VIA of the Periodic Table of the Elements. Preferred metals that can be present include molybdenum, tungsten, chromium, titanium, hafnium, zirconium, vanadium, tantalum, niobium, or combinations thereof.

The amount of alkaline earth metal promoter(s) and/or other metal promoter(s) deposited on the carrier is a promoting amount. The other metal promoter may typically be present in an amount from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, when measured as the metal.

Suitable non-metal promoter(s) may comprise elements from Groups IIIB, IVB, VB, VIB and VIIB of the Periodic Table of the Elements, and combinations thereof. Preferred but non-limiting examples include one or more sulfur compounds, one or more phosphorus compounds, one or more boron compounds, one or more halogen-containing compounds, or combinations thereof.

The amount of non-metal promoter(s) deposited on the carrier is a promoting amount. The non-metal promoter may typically be present in an amount from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, when measured as the element.

The silver solution used to impregnate the carrier may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on, or interaction with, the solvated promoters. Organic-based solvents that have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range from about 0.1% by weight up to the maximum solubility afforded by the particular solvent/solubilizing agent combination employed. It is generally very suitable to employ solutions containing from 0.5% to about 45% by weight of silver, with concentrations from 5 to 35% by weight of silver being preferred.

Impregnation of the selected carrier is achieved using any of the conventional methods; for example, excess solution impregnation, incipient wetness impregnation, spray-coating, etc. Typically, the carrier material is placed in contact with the silver-containing solution until a sufficient amount of the solution is absorbed by the carrier. Preferably the quantity of the silver-containing solution used to impregnate the porous carrier is no more than is necessary to fill the pores of the carrier. A single impregnation or a series of impregnations, with or without intermediate drying, may be used, depending, in part, on the concentration of the silver component in the solution. Impregnation procedures are described, for example, in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various promoting amounts of other components can be employed.

After impregnation of the carrier with the silver-containing compound, i.e., a silver precursor, a rhenium component, a cesium component, and the optional other components in promoting amounts, the impregnated carrier is calcined for a time sufficient to convert the silver containing compound to an active silver species and to sufficiently remove the volatile components from the impregnated carrier to result in a catalyst precursor. The calcination may be accomplished by heating the impregnated carrier, preferably at a gradual rate, to a temperature in the range from about 200° C. to about 600° C. at a pressure in the range from about 0.5 to about 35 atmospheres. In general, the higher the temperature, the shorter the required heating period. A wide range of heating periods have been suggested in the art; e.g., U.S. Pat. No. 3,563,914 discloses heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver is converted to the active silver species. Continuous or step-wise heating may be used for this purpose.

During calcination, the impregnated carrier may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Further information on catalyst manufacture may be found in the aforementioned U.S. Patent Publication No. 2007/0037991.

Epoxidation Process

The epoxidation process may be carried out by continuously contacting an oxygen-containing gas with an olefin, preferably ethylene, in the presence of the previously-described catalyst produced by the invention. Oxygen may be supplied to the reaction in substantially pure molecular form or in a mixture such as air. By way of example, reactant feed mixtures may contain from about 0.5% to about 45%, preferably about 5% to about 40% of ethylene and from about 3% to about 15% oxygen, with the balance comprising comparatively inert materials including such substances as carbon dioxide, water, inert gases, other hydrocarbons, and the reaction moderators described herein. Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process as well as common contaminants in the feed gases. Both have adverse effects on the catalyst, so the concentrations of these components are usually kept at a minimum.

Also present in the reaction are one or more halohydrocarbon moderators. Non-limiting examples include C1 to C8 halohydrocarbons individually, or in mixtures of two or more halohydrocarbons. Most preferably, the halogen in these halohydrocarbons is chlorine. Controlling moderator concentration level is particularly important with rhenium-containing catalysts. As mentioned previously, the present invention also makes use of a specific moderator control system.

A usual method for the ethylene epoxidation process comprises the vapor-phase oxidation of ethylene with molecular oxygen, in the presence of the catalyst, in a fixed-bed tubular reactor. Conventional, commercial fixed-bed ethylene-oxide reactors are typically in the form of a plurality of parallel elongated tubes (in a suitable shell) approximately 1.5 to 70 mm O.D. and 10 to 65 mm I.D. and 4-16 m long filled with catalyst. Such reactors include a reactor outlet which allows the olefin oxide, un-used reactants and byproducts to exit the reactor chamber.

In actual service, it is typical (especially for a rhenium-containing highly selective catalyst) to condition the catalyst in a "conditioning", "initiation", or "start-up" process before reaching typical operating conditions and producing commercial scale quantities of ethylene oxide. The present invention is not specific to any particular conditioning or start-up process; rather, the present invention makes use of the discovery that, when properly operated, the optimal moderator concentration in an epoxidation process has an exponential relationship with temperature. This correlation is valid over the temperature range of about 190° C. to 300° C. This temperature range is essentially the commercially relevant temperature range for a highly selective catalyst, although in practice most reactors for catalytic oxidation of ethylene to ethylene oxide operate in the preferred sub-range of 220° C. to about 280° C. Generally, temperatures below 220° C. are too low for the catalyst to produce ethylene oxide in the high yield typical of commercial production rates. On the upper end of the scale, 300° C. is about the highest temperature at which most reactors for catalytic oxidation of ethylene to ethylene oxide can operate and is about the highest temperature at which the catalyst can effectively perform.

In the present invention, the operator may decide to implement the moderator control procedure at any temperature in excess of 190° C., or in the preferred embodiment, in excess of 220° C. The first temperature at which the operator implements moderator control is designated as the first temperature, and the amount of moderator used at that temperature is designated as the first moderator concentration. The first temperature will be in the range of about 190° C. to about 300° C. (preferably, about 220° C. to about 280° C.). The first moderator concentration is determined by the operator based on specific parameters and circumstances. Preferably, the first moderator concentration will be tuned by the operator to optimize catalyst performance to the fullest extent possible. As above, with respect to specific start-up or initiation processes, determining the first moderator concentration for desired performance levels is done according to techniques known by persons of ordinary skill in the art; determining this first moderator concentration is not within the scope of the present invention.

When the temperature is increased from a first temperature to a second temperature, which will also be in the range of about 190° C. to about 300° C. (preferably, about 220° C. to about 280° C.), the amount of moderator to be applied at the second temperature is determined by the exponential relationship:

$$M_2 = M_1(1+r)^{T_2-T_1}$$

It is important to note that that this moderator adjustment relationship is independent of gas composition. However, in order for this relationship to correctly predict the desired moderator concentration value at each temperature, it is necessary that the first moderator concentration value be correctly determined to achieve optimum catalyst selectivity and activity. Since this first moderator concentration is dependent on the concentration of hydrocarbons in the feed gas, if the concentration of hydrocarbons in the feed gas is substantially changed during operation, then the inventive relationship still applies, but it is necessary to determine a "new" first moderator concentration from which the inventive relationship can then be further applied.

The second moderator concentration given by the inventive relationship will have the same basis as the first moderator concentration. For example, if the basis for determining the first moderator concentration is the weighted sum of all chlorohydrocarbons in the feed gas, then the basis for the second moderator concentration will also be the weighted sum of all chlorohydrocarbons in the feed. Provided that the first moderator concentration was that value that gave optimum catalyst performance at the first temperature, then the second moderator concentration will give optimum catalyst performance at the second temperature.

The operating pressure may vary from about atmospheric pressure to about 30 atmospheres, depending on the mass velocity and productivity desired. Higher pressures may be employed within the scope of the invention. Residence times in commercial-scale reactors are generally on the order of about 2 to about 20 seconds.

The resulting ethylene oxide, which exits the reactor through the reactor outlet, is separated and recovered from the reaction products using conventional methods. For this invention, the ethylene epoxidation process may include a gas recycle wherein substantially all of the reactor effluent is readmitted to a reactor inlet after substantially or partially removing the ethylene oxide product and the byproducts, including carbon dioxide and water.

The previously-described catalysts have been shown to be particularly selective for oxidation of ethylene with molecular oxygen to ethylene oxide especially at high ethylene and oxygen conversion rates. The conditions for carrying out such an oxidation reaction in the presence of the catalysts of the present invention broadly comprise those described in the prior art. This applies to suitable temperatures, pressures, residence times, diluent materials, gas compositions supplied to the reaction, moderators and moderator concentrations, and recycle operations, or applying successive conversions in different reactors to increase the yields of ethylene oxide. The use of the present catalysts in ethylene oxidation reactions is in no way limited to the use of specific conditions among those which are known to be effective.

For purposes of illustration only, the following are conditions that are often used in current commercial ethylene oxide reactor units: a gas hourly space velocity (GHSV) of 1500-10,000 $h^{-1}$, a reactor inlet pressure of 10-30 atmospheres, a coolant temperature of 190-300° C., an oxygen conversion level of 5-60%, and an EO production rate (work rate) of 100-450 Kg EO/($m^3$ catalyst h). The feed composition in the reactor inlet after the completion of start-up and during normal operation typically comprises (by volume %) 1-40% ethylene, 3-12% $O_2$; 0.3% to 20%, preferably 0.3 to 5%, more preferably 0.3 to 1% of $CO_2$; 0-3% ethane, an amount of one or more chlorohydrocarbon moderators, which are described herein, and the balance of the feed being comprised substantially of argon, methane, nitrogen or mixtures thereof.

EXAMPLE

The invention will now be described in more detail with respect to the following non-limiting example.

A rhenium-containing high selectivity catalyst matching the specifications stated herein was prepared. Then, a portion of this catalyst was charged into a reactor. The reactor was purged with dry nitrogen gas prior to introduction of the feed gas. The catalyst was then conditioned in a feed-gas mixture comprising ethylene, oxygen and ethyl chloride moderator, at a temperature of 250° C., following methods described in the prior art.

After conditioning the catalyst, the feed gas was set to a mixture of (by volume) 25% ethylene, 7% oxygen, 2% carbon dioxide, 1.0 ppm ethyl chloride, with nitrogen as the balance, at 21.4 atmospheres pressure, with no gas recycle. Temperature was controlled to maintain 2.2% (by volume) ethylene oxide in the reactor effluent stream, giving an ethylene oxide production rate of approximately 215 Kg EO/($m^3$ catalyst h).

Figure 1:
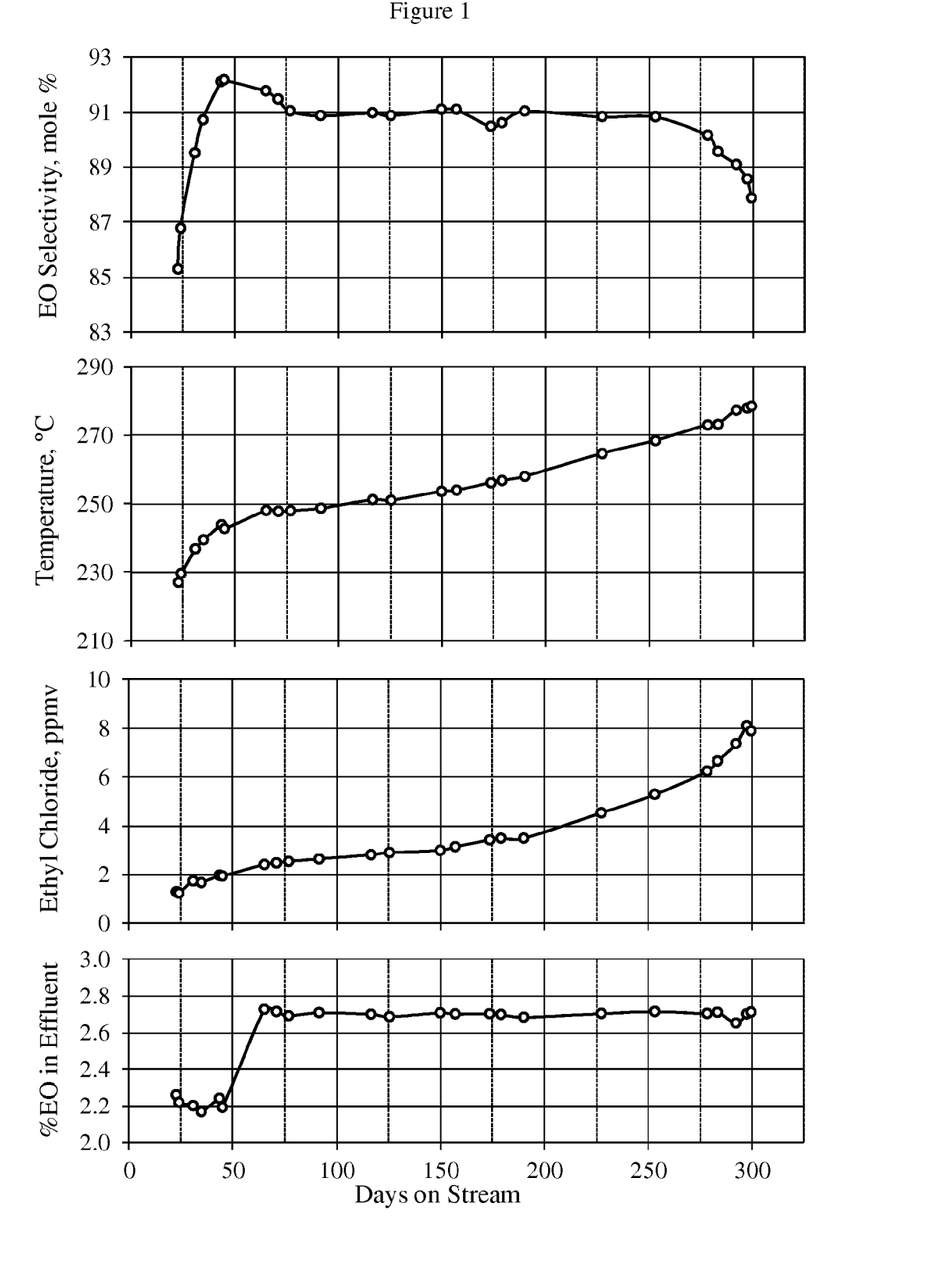
FIG. 1 is a graph of an EO catalyst run according to the Example.

Next, the ethyl chloride moderator concentration was adjusted to determine the first moderator concentration needed to give optimum catalyst performance. The first moderator concentration was determined to be 1.1 ppm, at the first temperature of 227° C. and an ethylene oxide selectivity of 85.5%. Then, throughout the duration of the test, temperature was increased to maintain the desired ethylene oxide production rate. When a change to a second temperature was required, the moderator concentration was immediately set to the second moderator concentration determined by the inventive relationship. In this way, optimum catalyst performance was maintained with the required temperature change. The most suitable value for the moderator control factor r was 3.9%. The test was continued for a period of 300 days. The test data are displayed in FIG. 1.

On day 44, the ethylene oxide concentration in the reactor effluent stream was increased to 2.7%, the gas flow rate was decreased, and the pressure was decreased to 18.0 atmospheres. The new ethylene oxide production rate was approximately 230 Kg EO/($m^3$ catalyst h).

Figure 2:
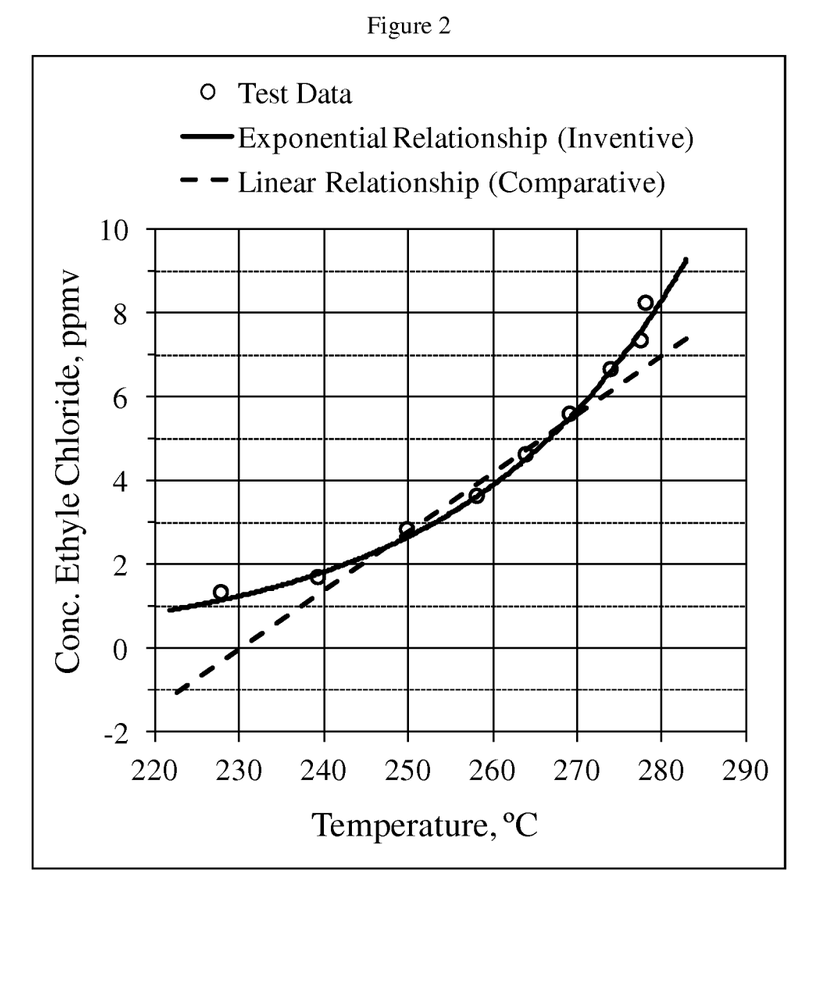
FIG. 2 is a graph of optimum moderator concentration based on the test data from the Example.

Based upon the test data, optimum moderator (ethyl chloride) concentration is plotted against temperature in FIG. 2. Throughout the entire operating temperature range, this chart shows that the relationship between optimum moderator concentration and temperature is well described by the inventive exponential relationship, using a moderator control factor r of 3.9%.

$$M_2 = M_1(1+r)^{T_2-T_1}$$

The comparative linear relationship given in FIG. 2 does not adequately describe the trend in the data. Therefore, optimum moderator concentration does not vary in linear fashion with temperature as taught in the prior art.

Figure 3:
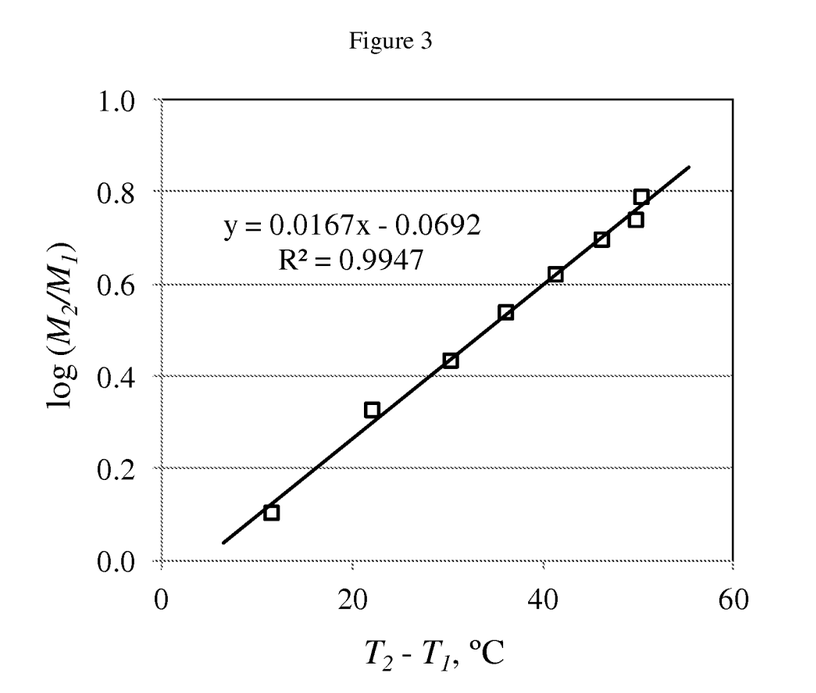
FIG. 3 is a graph for determining the moderator control factor r as according to the present invention based on data from the Example.

FIG. 3 illustrates the method taught in the present invention for determining the moderator control factor r. Based on the following form of the inventive relationship, $$\log\left(\frac{M_2}{M_1}\right) = (T_2 - T_1)\log(1 + r)$$

the slope of $\log(M_2/M_1)$ plotted against $(T_2-T_1)$ gives the best value of the moderator control factor r. From the linear regression analysis applied in FIG. 3, the slope of the best-fit line is 0.0167. The value of r is then determined algebraically, as follows:

$\log(1+r)=0.0167$ $1+r=10^{0.0167}=1.039$ $r=3.9\%$

This is the value of r that was used in the example.

It will be appreciated by those skilled in the art that changes could be made to the embodiments described above without departing from the broad inventive concept thereof. It is understood therefore that this invention is not limited to the particular embodiments disclosed, but it is intended to cover modifications within the spirit and scope of the present invention as defined by the appended claims.

We claim:

1. A method for the epoxidation of an olefin comprising:
reacting a feed gas composition containing an olefin, oxygen, and a halocarbon moderator having a first optimum moderator concentration $M_1$ in the presence of an epoxidation catalyst at a first temperature $T_1$;
increasing the first temperature to a second temperature $T_2$; and
increasing the first optimum moderator concentration to a second optimum moderator concentration $M_2$, wherein the second optimum moderator concentration is defined by the equation:

$M_2=M_1(1+r)^{T_2-T_1}$ wherein temperature has the units of degrees Celsius, and r is a constant factor which is in the range of from 0.001% to 100%.

2. The method of claim 1, wherein the value of r is from about 0.1% to about 10%.

3. The method of claim 1, wherein the olefin is ethylene.

4. The method of claim 1, wherein the first temperature and the second temperature are within a range of about 190° C. to about 300° C.

5. The method of claim 1, wherein the feed gas composition contains about 5% to about 40% of ethylene and from about 3% to about 15% oxygen.

6. The method according to claim 1, wherein the moderator is a chlorohydrocarbon or mixture of one or more chlorohydrocarbons selected from the group consisting of methyl chloride, ethyl chloride, ethylene dichloride and vinyl chloride.

7. The method according to claim 1, wherein the value of r is in the range of about 2% to about 8%.

8. The method according to claim 1, wherein the epoxidation catalyst comprises a carrier, at least a catalytically effective amount of silver or a silver-containing compound, a promoting amount of cesium or a cesium-containing compound, and a promoting amount of rhenium or a rhenium-containing compound.

9. The method according to claim 8, wherein the epoxidation catalyst further comprises a promoting amount of one or more alkali metals or alkali-metal-containing compounds.

10. The method according to claim 8, wherein the carrier comprises alpha-alumina.

11. The method according to claim 1, wherein the increasing the first optimum moderator concentration to the second optimum moderator concentration is independent of the feed gas composition.

12. The method according to claim 1, wherein the first optimum moderator concentration and the second optimum moderator concentration are both based on a total amount of all chlorohydrocarbons present in the feed gas composition.

13. The method according to claim 1, wherein the first optimum moderator concentration provides a first optimum catalyst selectivity and activity at the first temperature, and wherein the second optimum moderator concentration provides a second optimum catalyst selectivity and activity at the second temperature.

* * * * *